United States Patent
Weckström

Patent Number: 5,610,400
Date of Patent: Mar. 11, 1997

[54] SPECTROSCOPIC MEASURING SENSOR FOR THE ANALYSIS OF MEDIUMS

[75] Inventor: Kurt Weckström, Espoo, Finland

[73] Assignee: Instrumentarium Oy, Finland

[21] Appl. No.: 396,917

[22] Filed: Mar. 1, 1995

[30] Foreign Application Priority Data

Mar. 2, 1994 [FI] Finland ................................. 941001

[51] Int. Cl.⁶ ................................................. G01N 21/35
[52] U.S. Cl. ................................................. 250/345
[58] Field of Search ................................................. 250/345

[56] References Cited

U.S. PATENT DOCUMENTS

| | | |
|---|---|---|
| 3,121,790 | 2/1964 | Munday et al. . |
| 4,468,561 | 8/1984 | Speeter ................................ 250/345 |
| 5,054,869 | 10/1991 | Doyle ................................ 385/133 |
| 5,254,858 | 10/1993 | Wolfman et al. . |
| 5,282,473 | 2/1994 | Braig et al. ................................ 128/664 |

FOREIGN PATENT DOCUMENTS

| | | |
|---|---|---|
| 286419 | 10/1988 | European Pat. Off. . |
| 447931 | 9/1991 | European Pat. Off. . |
| 740374 | 11/1955 | United Kingdom . |

*Primary Examiner*—Constantine Hannaher
*Attorney, Agent, or Firm*—Andrus, Sceales, Starke & Sawall

[57] ABSTRACT

The object in a non-dispersive gas sensor is to minimize the use of moving parts, as those reduce the service life of a sensor. A preferred solution is such that it includes one infrared source (1), one short sample chamber (2) and one or generally more infrared detectors (9) operating over a certain wavelength band. If the number of detectors is more than one, it is important that the light arriving in all detectors has traveled through the sample chamber (2) as identically as possible. However, in view of using preferred commercial detectors without major angular errors and delay times in signals, the light is guided from the source (1) to the detector (9) by means of a wave tube (7)

19 Claims, 3 Drawing Sheets

SPECTROSCOPIC MEASURING SENSOR FOR THE ANALYSIS OF MEDIUMS

The present invention relates to a measuring sensor for the spectroscopic analysis of mediums, said measuring sensor comprising a sample chamber for a medium to be analyzed, said chamber being provided with at least two radiation transmitting windows or window sections in window openings included in the chamber, a radiation source for emitting radiation which progresses through the first window, the sample chamber and further through the second window, one or a plurality of detectors which is or are optically directed towards this second window or window section, as well as a filter permeable to a certain wavelength band between said opening of the second window and each detector.

When analyzing mediums, typically gases, for example by means of infrared technology, the most preferred solution has proved to be a non-dispersive measuring method which involves analyzing each gas component in a gas sample to be examined, i.e. identifying a gas component and/or measuring its concentration by using a specific spectral band pre-assigned to each. The multi-gas sensor typically consists of a radiation source, such as a wide-band infrared radiation source, a sample chamber, mechanically replaceable narrow-band filters, and an infrared detector. This type of solution is disclosed for example in the publication U.S. Pat. No. 4,233,513. A problem in such a solution is a short service life caused by the wearing of moving parts. In addition, the solution requires relatively high-speed detectors. Such detectors capable of operating at room temperature are hard to find when the value of a wavelength to be detected exceeds about 5 µm. It is generally known that most of the characteristics bands of infrared absorption lie within these very wavelengths, for example within the range of 8–14 µm, although substantially shorted wavelengths, e.g. down to 3 µm, are used as well. For the above reasons, there is an increasing tendency to avoid solutions that include moving parts. However, the above-described solution has provided a benefit of having a path of rays through the chamber common to all measuring bands and a single detector has been sufficient for detecting all rays. Thus, the commensurable changes, including for example the contamination of a sample chamber and thermal sensitivity of a detector, which have exactly the same effect when using different wavelength bands, have been easy to compensate for. In a sensor operating without moving parts, each wavelength band must be provided with an individual detector and, thus, a plurality of detectors are required. The current detectors, for example thermocouple detectors, are very similar in terms of the properties thereof and, therefore, the compensation required because of the disparity thereof does not generally cause problems. On the other hand, the fact that radiation to various detectors travels through the sample chamber over different routes may lead to measuring errors, particularly if the chamber windows or walls become stained. This is a common type of problem e.g. in respiratory gas analyzers. The publication U.S. Pat. No. 5,081,998, discloses a solution, wherein the detectors along with their filters are side by side, although the cited publication is principally concerned with the elimination of the effects of thermal noise and a change of the operating location. This prior solution is not at all capable of compensating for other commensurable errors, such as an error caused by the uneven contamination of a sample chamber, since the rays to various detectors travel completely separately from each other. The problem becomes even more serious if the number of gas components to be measured were more than two. In the cited publication, the detector systems measuring the bands employ adjoining parallel radiation but, even if the detectors were directed towards the centre of an infrared source, this does not solve the problem especially when a plurality of detectors are used. Thus, also the angle between various optical paths increases and a possibility of using the same path through the sample chamber decreases further. The distance can be increased and hence the angle reduced, but in that case the light intensity decreases too much.

Another possibility of attempting to solve the above problems is to use specially designed detector cells, comprising a plurality of detectors and corresponding filters packed tightly adjacent to each other. This type of solution is disclosed in the publication U.S. Pat. No. 4,772,790. In this case, the rays progressing through a sample chamber are roughly similar to all detectors and, thus, the commensurable errors are nearly compensable. In practice, however, the solution is expensive and vulnerable. If just a single individual component is defective, the entire detector cell must be replaced. This solution may also lead to problems when it is necessary to substantially increase the number of detectors, since the cell will have such a large surface area that a portion of the radiation passed through the sample chamber and received by the various detector elements therein has distinctly originated from different parts of the chamber. If the structure set forth in this publication is to be provided with interference filters upstream of the detector elements, the radiation source must meet strict requirements as these filters require a substantially orthogonal incident radiation for maintaining a precise band transmission, whereby no scattered radiation should be present. The cited sample chamber and other structure do not contribute to the creation of parallelism in radiation.

In view of using spaced-apart narrow-band filters and detectors which all see the infrared source from the same direction and all rays detected thereby have traveled through the sample chamber over a substantially common path, use has been made of beam splitters. The publication U.S. Pat. No. 4,914,719 discloses one such multi-gas analyzer. However, the measuring system is complicated and expensive. In addition, the light intensity is inequal and quite low for different detectors, on the one hand, because the distance to an infrared source is different therefor and, on the other hand, because the preceding half-mirrors take some of the intensity. In principle, the reflectivities of successive half-mirrors could be adapted to be gradually varying for producing the same intensity for various detectors but this increases the price even further and the low level of intensity still remains a problem, especially if the use of several detectors is necessary. In the arrangement disclosed in this cited publication, it is difficult and expensive to maintain the individual detectors at the same and constant operating temperature, since the distances therebetween are long and such distances cannot be reduced without problems.

An object of this invention is to eliminate the above problems. Accordingly, one object of the invention is to provide such a non-dispersive measuring sensor for the spectroscopic analysis of gas mixtures and other mediums, such as liquids and solid radiation permeable materials, in which sensor the commensurable errors are simple to compensate for or do not occur at all and whereby the rapid concentration changes of a gas mixture are precisely and immediately measurable. Thus, the objective is a sensor, wherein the intensities over different wavelength bands are measured simultaneously and wherein the radiation for individual detectors in the sensor originates as accurately as possible from the same point through a sample chamber and wherein each sensor sees a radiation source as precisely as possible in the same or a corresponding way. A second object of the invention is a measuring sensor of the above type, wherein the bandpass filters upstream of the detectors are provided with a radiation as parallel as possible and thus with a precise and correct band transmission, even if the radiation source emitted also diffused radiation or a gas mixture to be measured were of a type to cause the diffusion of radiation. A third objective of the invention is such a measuring sensor which is capable of providing each of a plurality of detectors, the number of which can be typically 4–7, with a constant high radiation intensity. Thus, the radiation and especially the long-wave infrared radiation must not be suppressed or distributed between the sample chamber and the detectors. A fourth objective of the invention is such a sensor, wherein the individual detectors can be maintained in a simple manner at a stable constant temperature. A still further objective of the invention is a measuring sensor of the above type which would be simple and economical to manufacture.

The above problems can be resolved and the above objective are achieved by means of a measuring sensor of the invention which is characterized by what is set forth in the appended claims and by means of a method which is characterized by what is set forth in the appended claims.

The solution is based on the utilization of a light guide in the form of a wave tube. The term wave tube refers to an elongated light carrying hole or cavity, having walls made of a material capable of reflecting light. It differs from the optical fiber in that the propagation of light is not based on the utilization of total reflection but on a high reflectivity of the walls. A benefit gained by this structure is for example that light need not travel in a medium optically more dense than the wall material, such as the glass core of an optical fiber. Thus, even the long-wave infrared radiation propagates with minor losses in a wave tube. The reflection losses are not generally of a major significance as the tube is relatively short. The ratio of length to diameter may be as low as 2, but usually at least 5, and in a preferred solution of this invention it is in the order of 10–30. The walls have a reflectivity which in practice limits the maximum length to about a meter, and a preferred length is in the order of 30–100 mm. If the detector elements can be made very small, it is possible to employ wave tubes even shorter than this as long as they have a sufficient length relative to the cross-dimensions thereof, as defined above. The wave tube, which in practice comprises an elongated hole made in a suitable material, carrier the light almost without losses from the sample chamber outlet to individual detectors. The solution enables the simultaneous use of a plurality of standard type detectors and, since the distance from an infrared source to a detector can be relatively long as compared to the distance between detectors, the path of light through the sample chamber is roughly the same for all detectors and all detectors are provided with a similar visual field over the radiation source. Most preferably, the wave tube is not flexible as bending alters the path of light within the tube and, thus, has a disturbing effect on the amount of light arriving in the detector.

While using effectively the reflections from the tube walls for carrying e.g. infrared radiation to detectors, said wave tube has an effect reducing to some extent the divergence or stray radiation of a light beam, which is beneficial and even inevitable when using narrow-band interference filters. This feature of a wave tube is a result of the fact that smaller angles of incidence towards the tube wall cause more losses than larger angles of incidence, the expression angle of incidence referring to an angle between the incident ray and the normal of a surface, as established in the art of optics. A suitable material selection can have an effect on the angle-losses relationship, in other words, on the angular distribution and thereby on the parallelism of radiation arriving in a filter included in the detector. Most of the radiation reflects inside a tube at a very large angle of incidence and, thus, the losses are low almost regardless of the material selection. A longer distance between an infrared source and a detector is preferred also in terms of thermal design, since the thermal load induced by convection of the source is then easy to control for example by means of a heat insulation. At the same time, all detectors can be readily anchored on the same thermal mass as the detectors are located close to each other. This divergence reducing feature in a wave tube of the invention is not only capable of reducing problems cause by possible stray radiation, such as a source of stray radiation, and relating e.g. to the above-mentioned requirement for the direction of incidence of radiation set on otherwise preferred interference filters but, as a result thereof, such a wide-surface diffused-radiation emitting radiation source can be made even beneficial since, in certain cases, it is capable of producing a radiation source which is identically visible for the individual detectors of a sensor.

The invention will now be described in detail with reference made to the accompanying drawings.

Figure 1:
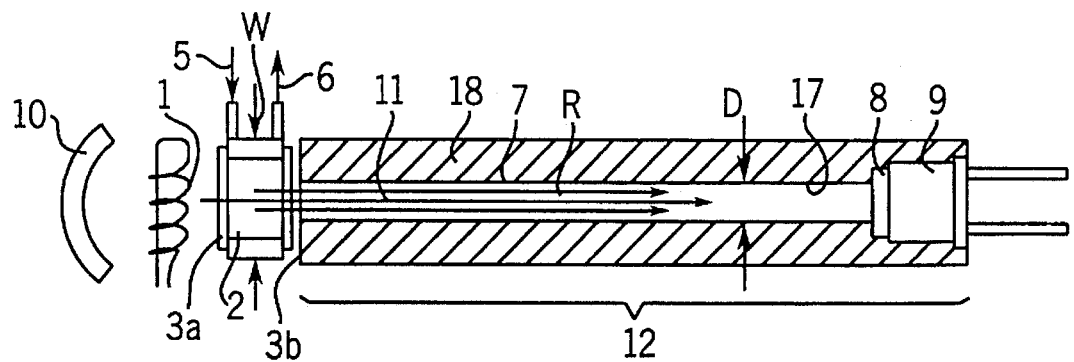
FIG. 1 shows the simplest embodiment for a measuring sensor of the invention.
Figure 2:
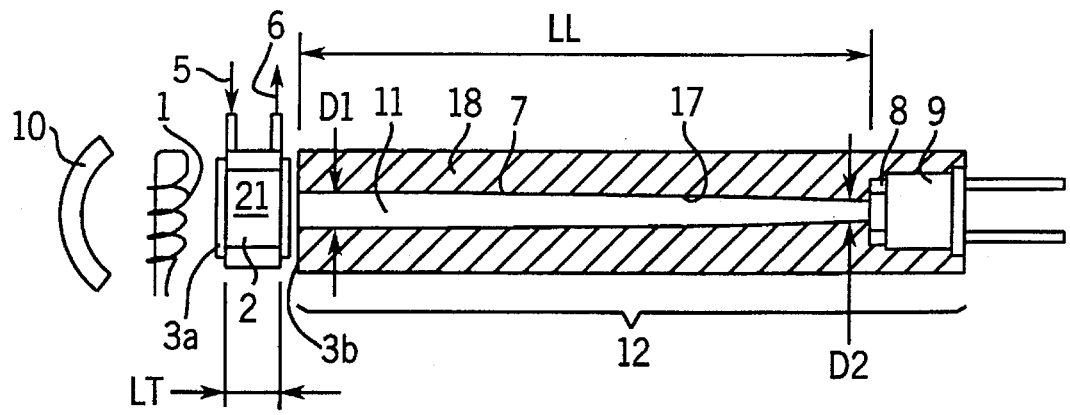
FIG. 2–3 show two further embodiments for a measuring sensor of the invention.
Figure 3:
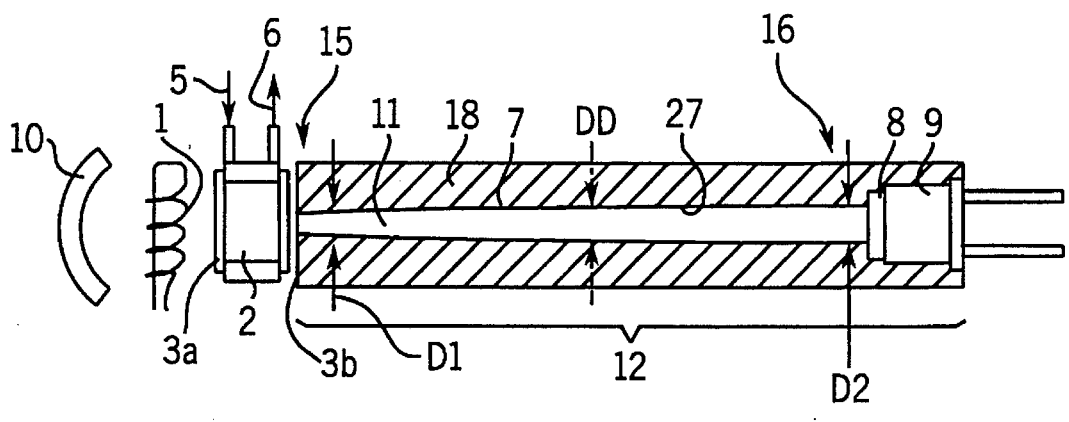

The basic solution shown in FIGS. 1–3 comprises typically an infrared-radiation emitting radiation source 1, a sample chamber 2 provided with windows 3a and 3b transmissive to this infrared radiation and located opposite to each other on different sides of the chamber, and inlet and outlet connections 5 and 6 for a gas sample, a wave tube 7, a narrow-band filter 8 and an infrared detector 9. The chamber windows 3a and 3b or a possible single window are set in corresponding window openings or an opening, included in the chamber and forming parts thereof. The windows may consist of filters or the like, as described subsequently in this specification. A medium 21, e.g. a sample gas 21, flows by way of the connections 5 and 6 through the sample chamber 2 and the flowing gas batch may be either an entire gas volume bound for an object not discussed in this specification or a small sample picked up therefrom. The radiation originates from this infrared source, propagates by way of the first window 3a, through the sample chamber 2 and the contained gas 21 to be analyzed, further by way of the second window 3b into the wave tube 7, through the filter 8 and into the radiation detector 9. The infrared source comprises usually a wide-spectrum incandescence, behind which can be a reflector 10 for an improved radiation capacity. In a structure of the invention, the radiation source 1 can be wide in a direction transverse to the above-described radiation traveling direction R, for example equal to or even wider than the sample chamber width W by virtue of the very wave tube but the use of a smaller or spot-like radiation source enables the use of a wave tube 7 which is shorter and/or has an improved operating efficiency depending on the configuration. In this invention, the sample chamber 2 has in the radiation traveling direction R a short length LT but, in the case of a single wave tube, it could also be long. The short sample chamber refers to a chamber having a length LT which is at least less than twice its width W and typically less than the width W. The long sample chamber, wherein the length LT is thus more than twice its width W, would also function as a wave tube but, according to this invention, the wave tube 7 is not intended to contain any sample gas. When the question is about a respiratory gas sensor, the suitable chamber length is for example 3 mm–10 mm.

The anesthesia gases, such as halothane, enflurane, isoflurane, sevoflurane and desflurane, are measured within the above-mentioned range of 8 µm–14 µm while the detection of carbon dioxide and nitrous oxide gas is generally effected within the range of 3,8 µm–4,2 µm. The sample chamber windows 3a and 3b can be made of a material transmissive to the infrared radiation to be measured, such as calcium fluoride, or one or both of the windows can be filters having a wide band in terms of transmission and intended to eliminate the unnecessary radiation outside the wavelength range, which may cause heating of the detector arrangement. The second window 3b can also be a required filter transmissive to the wavelength band but generally it is appropriate to include filters 8, 8a, 8b, ... 8i ... in either end 15 or 16 of a wave tube 7, 7a, 7b, ... 7i ... for enabling the use of a variety of wavelength bands and, thus, for analyzing a plurality of material components from a medium to be examined.

The wave tube 7 carrier the infrared radiation from its first end 15 facing the outlet window 3b of said sample chamber 2 to a filter-detector pair 8, 9 adjacent to its second end 16. The wave tube 7 can preferably be a hole 11 drilled and smoothed in aluminium, but it could also be made of some other highly reflective metal, such as copper, or the hole 11 could have its walls 17 coated with a reflective metal foil 27, such as a gold layer or an interference-based multilayer mirror 27, as depicted in FIG. 3. The wave tube body material 18 may also consist of a polymer material, glass, mineral or some other suitable solid non-metal or compound. Such non-metals and minerals may include silicon, calcium fluoride, various borides, nitrides and oxides etc. Thus, the wave tube is provided with an envelope surface 17, reflecting towards its internal cavity 11 and possible consisting of an actual mirror surface 27 or, as generally defined, a body material 18 having an index of refraction which exceeds that of the wave tube care portion, i.e. interior of the hole 11. The wall has a reflectivity which at large angles of incidence is easily in the order of 0.9 or more and, thus, the losses in practice are minor. In this context, the angle of incidence refers to an angle between the normal of a surface and the incident ray, as generally understood in the field of optics. The ratio of a wave tube length LL to its diameter D, to a first end diameter D1, to a second end diameter D2 or to a mean diameter DD can be as low as 2, generally however at least 5, and in a preferred solution of this invention it is in the order of 10–30. The walls have a reflectivity which in practice limits the maximum length LL to about a meter and a preferred length LL is in the order of 30–100 mm. If the detector elements can be made very small, it is possible to employ even shorter wave tubes 7 as long as they have a sufficient length relative to the cross-dimensions thereof, as described above.

Since polymeric materials and glass as well as most minerals have a poor reflection of light except for very large angles of incidence, it is thus quite easy to effect a sort of restriction for the angular distribution of light, which principally accepts radiation having an angular distribution of less than R+/–10°, wherein the radiation direction R is said principal direction of a ray passing through the sample chamber and the wave tube which is the same as any given direction of the wave tube centre axis and normally orthogonal to the detector 9 and the plane of its filter 8. If, for example, the ratio of tube length to diameter is 20, the radiation traveling at the angles of R+/–5° has a transmission in this wave tube of about 50%, the radiation traveling at the angles of R+/–10° has a transmission of 6%, and the radiation traveling at the angles of R+/–20° is no longer more than 0.001%. It is prior known that the narrow-band interference filter 8 is sensitive to the angle of incidence of light in such a manner that the transmission band or passband shifts towards a shorter wavelength when the angle of incidence increases to exceed about 10°. This behaviour is not generally desirable in gas analyzers since then the transmission band is indefinite and possibly also instable and susceptible to faults. The interference filter 8 has a band width which is normally about 1%–5% of the mean wavelength and selected on the basis of absorption points produced by a sample gas in the infrared spectrum. Thus, when the angular distribution is relatively high, e.g. R+/–20°, the rays arriving at wide angles are reflected several times from the wave tube wall 17 and the more times the wider the angle is. At the just mentioned angle of +/–20°, the ray is reflected in a wave tube of the invention at least two times and preferably at least four-five times for an effective damping or suppression. Thus, the above-described uncoated wave tube 7 of plastics or glass enables a very small angle of incidence to the interference filter 8, even when using a wide-surface radiation source 1. On the other hand, the use of a spot-like radiation source 1 emitting radiation directed therefrom hardly requires this feature of a wave tube in the presently described embodiment of the invention.

The filter 8 may comprise a separate component between the wave tube 7 and the detector 9 but it could also be integrated in the detector 9 for example as a radiation transmissive window therefor, as in FIG. 2. In any case, a single filter 8 and detector 9 produce at any given time a filter-detector pair for providing a non-dispersive measuring method. For each filter-detector pair 8a and 9a; 8b and 9b; ... 8i and 9i ... the filter can be mounted on either end of a wave tube, either on the end 15 adjacent to the sample chamber or at the end 16 adjacent to the detector. The space 11 within the wave tube 7 consists normally of air but it can sometimes detrimentally absorb infrared radiation to be analyzed, for example when it contains a great deal of the same gas to be measured as the sample chamber 2 or if it includes such a gas component which absorbs over the same wavelength range as any of the gases to be analyzed. In that case, the gas volume in the space 11 can be replaced by vacuum or such a gas which does not absorb over adverse wavelengths or the wave tube interior can be provided with a suitable absorbent, such as silica gel, zeolite or activated carbon. When the question is about carbon dioxide, it is also possible to use well-known calcium hydroxide as an absorbent. The interior 11 can also be supplied with a gas or a gas mixture which is present in the sample chamber as an interfering component. In this case, the interior 11 of the wave tube 7 operates as a sort of infrared absorption filter for this gas component. In these cases, the wave tube interior 11 is attempted to be sealed as tightly as possible and it is also conceivable that this gas be maintained in the interior at a pressure higher than that of the ambient air. In practice, the window 3b included in the wave tube adjacent to the sample chamber 2, or a filter located adjacent to this window in a manner not shown in the figures, may at the same time seal the first end 15 of a wave tube and, at the second end 16 thereof, the filter 8 and/or the detector 9 can be tightly attached to the tube 11 and seal it. It is obvious that the ends 15, 16 of the wave tube 7 can also be provided with their own infrared radiation transmissive windows which, if desired, can also serve as filters blocking unacceptable radiation wavelengths, as described above in reference to the sample chamber windows 3a, 3b. Optionally, the wave tube can also be completely open provided that there are no external disturbances.

Referring to FIG. 1, the wave tube interior surface 17 has the shape of a straight circular cylinder. Although the wave tube 7 preferably comprises such a cylindrical hole with its diameter designated by reference D, it could also be a cavity converging towards the detector, as shown in FIG. 2 in a second embodiment of the invention. A virtue of this solution is an improved radiation collecting capacity. However, the angular distribution of radiation in the vicinity of the detector exceeds that experienced in the case of FIG. 1, i.e. more radiation is also received from directions other than the medial direction R and, thus, it is only applicable to cases in which the filter 8 is not critically dependent on the radiation angle of incidence. In the embodiment shown in FIG. 3, the wave tube 7 is divergent towards the detector 9. This time the angular distribution in the vicinity of the detector is less than in FIG. 1, i.e. radiation is only received essentially in the medial direction R orthogonal to the filter 8 but, at the same time, the tube diameter has increased to such an extent that the collection of the entire signal requires a larger filter 8 and detector 9 than before. In these cases, the first end 15 of a wave tube has a diameter designated by reference D1 and that of the second end by reference D2. The mean diameter is DD, as schematically depicted in FIG. 3. The wave tubes may have a cross-sectional shape also other than circular, but a circular shape is the most preferred in terms of the efficiency of radiation passage. The first end 15 of the wave tube 7 has a cross-sectional surface, i.e. the cross-sectional surface corresponding to diameter D1, which is approximately equal to the cross-sectional outlet surface of the second window 3b or smaller than this cross-sectional outlet surface.

Figure 4:
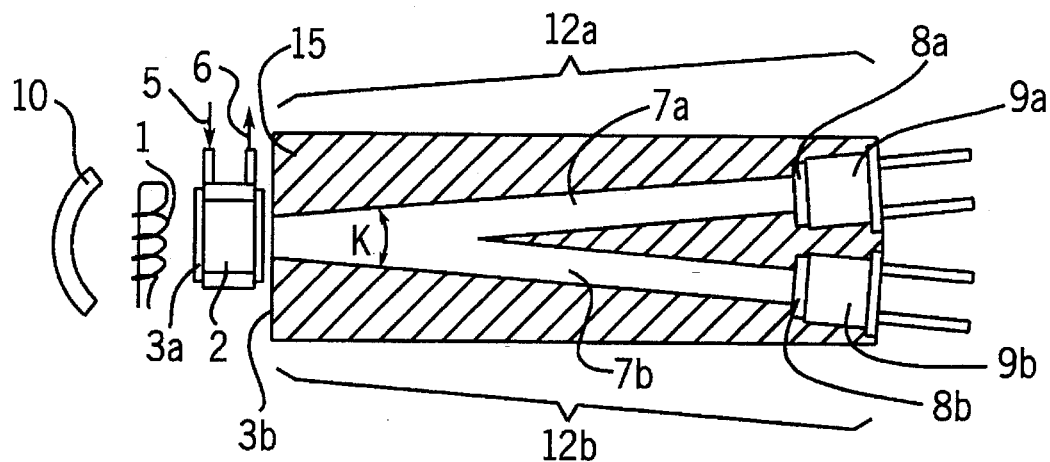
FIG. 4 shows a third embodiment for a measuring sensor of the invention, including two filter-detector pairs.

FIG. 4 shows a gas sensor provided with two wave tubes 7a and 7b and, respectively, two narrow-band filters 8a and 8b and two detectors 9a and 9b which make up filter-detector pairs 8a, 9a and 8b, 9b. Both wave tubes 7a and 7b are directed towards an infrared source 1 or at least between the source and the centre of a sample chamber 2, the first ends 15 or inlet ends of both wave tubes 7a and 7b being aligned with essentially the same surface section of the second window 3b for delivering the same radiation intensity into each wave tube and further to the respective filter-detector pair. Thus, between these two wave tubes 7a and 7b there is a small angle K whose bisector is typically orthogonal to the plane of the second window 3b. The wave tubes 7a, 7b may preferably be in the form of cylindrical holes but a converging or, respectively, a diverging type, as shown in FIGS. 2 and 3, is also possible. Particularly in this case, the sample chamber 2 has preferably a short length LT in view of carrying the rays for both wave tubes as accurately as possible along the same path through the chamber. Hence, the error caused by tainting of the chamber 2 is commensurable in both detectors and thus compensable without inducing an error in the measuring result. Thus, one wave tube system 12a can be used for rectifying the signal of another wave tube system 12b. In this context, the wave tube system 12 refers to a unit, comprising an assembly consisting of the wave tube 7 and the respective filter 8 and detector 9.

When using commercially available detectors 9, those are mounted in a TO-5-capsule having a maximum diameter of about 10 mm. If the distance to an infrared source is 70 mm, there is an angle K of about 8° forming between the wave tube systems 12a and 12b. If the infrared source 1 is located near the sample chamber 2 and the wave tube systems 12a and 12b are directed towards the same section in the front edge of source 1 or in the inlet widow 3a of sample chamber 2, the rays bound for the different wave tube systems have a deviation of about 0,4 mm in a lateral direction W at the window 3b of chamber 2, if the chamber length LT is 3 mm. The error caused by this minor deviation for example in a light beam having a diameter of 3 mm is negligible, presuming that the window 3b becomes inhomogenously tainted. The effect achieved is even less, if the wave tube systems 12a and 12b are directed towards the centre of sample chamber 2 but, in that case, the infrared source 1 may be partially screened or slightly different parts thereof may be visible for the different wave tube systems, but even these differences are quite negligible. In this very respect, an advantage is gained by the radiation source 1 having a large surface area and, thus, emitting diffused or scattered radiation and by wave tubes of the invention and especially by the divergence-reducing embodiments thereof, i.e. plastic, glass or other such uncoated wave tubes. Thus, a large-surfaced and hence a relatively homogeneous radiation source supplies both wave tubes essentially always with equal radiation, even if the focusing surface areas of the wave tubes in radiation source 1 were not exactly the same but, instead, the focusing had been effected on said second window 3b. As a comparison, it may be noted that a similar focusing on the second window at an angle K/2 when using a spot-like well directed light (as in the publication U.S. Pat. No. 4,772,790) would lead to a considerable screening of the radiation source since this type of radiation source emits almost no intensity beyond its centre axis. Despite this diffused light source, the wave tube of the invention is capable of supplying the filter-detector pairs 8a, 9a and 8b, 9b of a sensor effectively with orthogonal radiation. According to FIG. 4, the wave tubes 7a and 7b merge together at the end 15 adjacent to sample chamber 2. Thus, the interior 11 of said wave tubes is common to both branches and, thus, the above-mentioned possible special treatment of a gas can be readily performed. The wave tubes 7a and 7b have lengths which are preferably equal but, if necessary, could just as well differ from each other without major differences in light dissipation. It is obvious that the wave tubes 7a and 7b can have different capacities but, in that case, the distance therebetween is slightly longer and the possibility of rectifying commensurable errors is slightly more limited.

Figure 5:
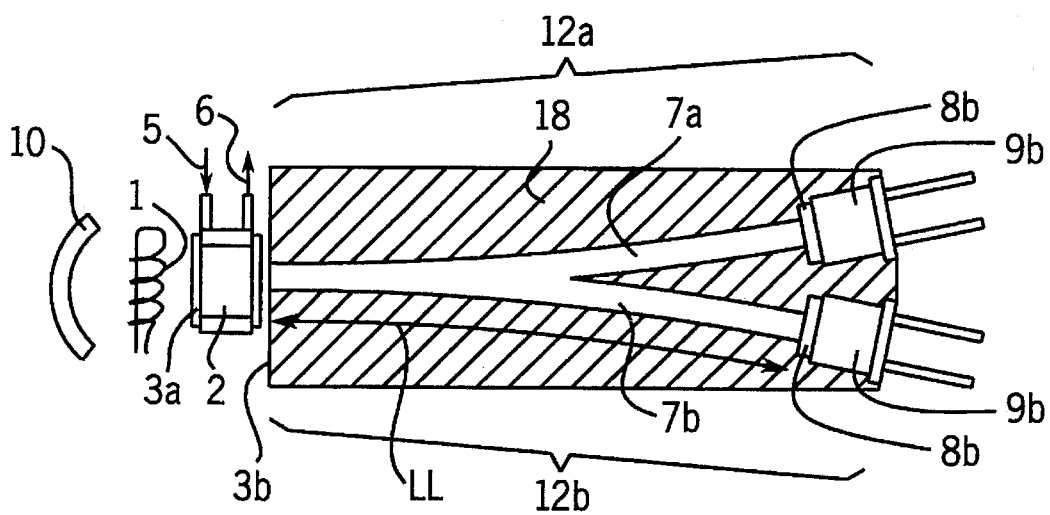
FIG. 5 shows a fourth embodiment for a measuring sensor of the invention, including two filter-detector pairs as well as curved wave tubes.

FIG. 5 shows one way of reducing the angular deviation described in the preceding paragraph and existing at the sample chamber 2. In this figure, the wave tubes 7a and 7b are not straight but outwardly curved, and usually curving outwards from the medial normal of the second window 3b. This way, the angle of departure relative to the first end 15 of a wave tube becomes very small while providing sufficient space for the filter-detector pairs 8a, 9a and 8b, 9b. Such wave tubes could be produced for example by casting or by bending straight tubes. The angular distribution of light increases a little at the detector 9, i.e. more radiation arrives also from directions other than the medial direction R as a result of bending the wave tube 7a, 7b and, therefore, the application of this embodiment requires the use of such a wavelength-band filter 8a, 8b which is not critically dependent on the angle. As described in reference to the preceding embodiment, also this embodiment, which comprises a plurality of wave tube systems 12a, 12b, includes just one wave tube volume 11 both for bringing the systems close to each other in view of eliminating commensurable errors and for enabling a simple gas filtering. In other respects, what was described in connection with the preceding embodiment applies to this embodiment as well.

Figure 6:
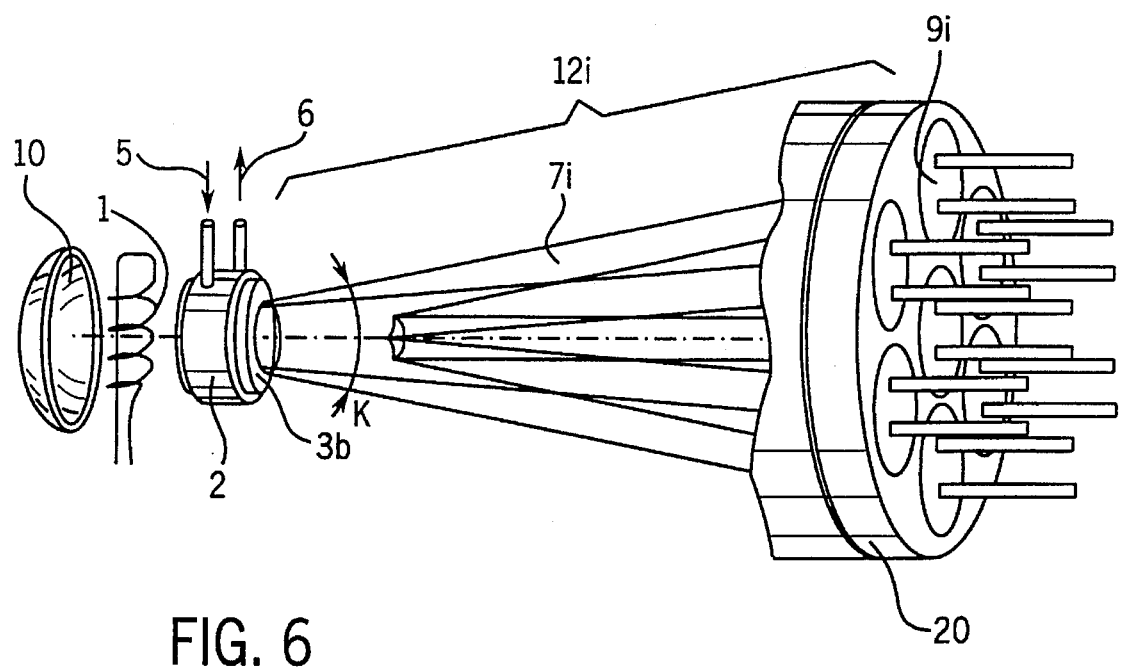
FIG. 6 shows a fifth embodiment for a measuring sensor of the invention, including seven filter-detector pairs for the analysis of a plurality of gas components.

The above embodiments relate to the use of two wave tube systems. FIG. 6 depicts a multi-gas analyzer of the invention, comprising seven wave tube systems generally designated by reference 12i, wherein i=a . . . g, and the corresponding wave tubes by reference 7i and detectors by reference 9i. Naturally, the system also includes a filter 8i corresponding to each detector 9i, but those are not visible in the figure. One of these systems 12i can compensate for the commensurable errors of other systems. As in the preceding embodiments relating to a plurality of wave tube systems, this one also has all wave tube systems 12i, and hence especially the filter-detector pairs 8a, 9a; 8b, 9b; 8c, 9c . . . thereof, positioned side by side relative to the radiation coming out of the second window for carrying the radiation delivered from the sample chamber 2 along the wave tubes 7a; 7b; 7c . . . in a substantially equal manner to each filter-detector pair. The divergence of rays bound for the wave tube systems at the sample chamber window 3b is now slightly more than in the arrangement of FIG. 4, but the errors are not very significant even now. The error can be reduced by extending or bending the wave tubes 7i, if this is permitted by the overall size of an analyzer. In other respects, all that was described in reference to the preceding embodiments applies to this embodiment as well. Preferably, each assembly of one filter 8i, wave tube 7i and detector 9i is used for analyzing one component of a medium, such as a gas mixture, i.e. for identifying the type or quality of said component and/or for determining the concentration thereof. In this case, the filter can be included in either end 15 or 16 or a wave tube or in the middle of a wave tube. Of course, it is possible to analyze a plurality of gas components by providing each individual wave tube with a plurality of sensors and/or filters, as described hereinafter.

When a plurality of filter-detector pairs are used for measuring many different gases, this arrangement provides the further advantage that all systems 12i or, in more simple cases, the systems 12a and 12b are in thermal equilibrium relative to each other by being in contact with the same element 18. This benefit can be emphasized by using a continuous metal element 20 or a like for fastening the detectors 9a; 9b; 9c . . . thereto, especially in cases that the wave tubes 7a; 7b; 7c . . . are made of plastics or glass or some other material having a poor thermal conductivity. If necessary, the detectors 9 can be maintained at a constant temperature by means of a thermostat not shown in the figures. In addition to this, all detectors 9i receive a sufficiently powerful signal and a change in the concentration of the components included in a gas sample contained in the sample chamber 2 is simultaneous in all detectors. This has a major importance in signal processing. Even a slight time delay between the individual detectors 9i easily results in a major error in the concentration and even the identification of a gas component may fail.

It is obvious that the above-described embodiments can be modified by using prior art solutions. Thus, for example, it is possible to include several, for example two, three of four filters and respective detectors, i.e. filter-detector pairs, in each detector unit corresponding to the above-described detector 9. Thus, the embodiments of FIGS. 4 and 5 could include four, six or eight filter-detector pairs. The device described in this specification can be used for analyzing gas mixtures, which refers to the identification of mixture components presumed possible and/or determination of the concentration of a known mixture component. The former is effected by selecting transmission bands for the filters 8 as desired and the latter by using the detectors 9 for measuring the absorptions occurred in radiation intensity, i.e. the intensities over certain wavelength bands, and by calculating on the basis thereof in a per se known manner the concentration of each desired gas component in a gas mixture. In principle, the wave tube interior 11 may consist of a material other than a gas, whether liquid or solid, as long as its index of refraction is sufficiently lower than that of the wave tube body 18 or coating 27 and said material is highly permeable to the wavelengths to be measured. Usually, this type of solution is not appropriate.

The medium 21 to be analyzed in the sample chamber 2 can be a gas, liquid, vapour or solid material. The measuring procedure is basically the same in all cases with the exception that the treatment of a very high viscosity liquid may require its own special measures in terms of the structure and dimensioning of a sample chamber. The analysis of a solid medium does not necessarily require an actual sample chamber at all or at least the windows 3a and 3b are not necessary. An object of the invention is to cover these applications as well regardless of whether or not the embodiment is indeed provided with solid windows. Thus, the expression first and second window is also intended to cover any limited volume or surface, which is permeable to desired radiation and on the other side of which is located a radiation source 1 or, respectively, a wave tube 1 along with its detector 9. These windows 3a and 3b can be included in the sides of a sample chamber 2 opposite to each other, as in the embodiments shown in the figures, or such windows can be included in the diverging sides of a sample chamber, the radiation propagating in such sample chamber for example by way of a mirror surface. In this case, the sample chamber could be a triangle, which is right-angled in a section taken in the radiation advancing direction and whose legs are windows and hypotenuse is a mirror surface. Other configurations are also conceivable. It is also possible to use just a single window provided, for example, with adjoining window section, the radiation passing through the first section into a sample chamber, reflecting from the opposite chamber wall, and traveling through the second window section and further into a wave tube, filter and detector or to a plurality of filters, wave tubes and detectors. Between the second window or window section and the wave tube and/or between the wave tube and the detector, respectively, may be fitted a prism, prisms or fiber optics or the like for deflecting the direction of a ray or rays, if necessary, in view of providing e.g. a desired shape and size for the measuring sensor. In all these configurations, the detector or detectors are optically directed to the second window 3b or second window section.

I claim:

1. A measuring sensor for the spectroscopic analysis of mediums, said measuring sensor comprising:

a sample chamber (2) for a medium to be analyzed, said chamber being provided with at least two radiation transmitting windows (3a, 3b) or window sections in window openings included in the chamber;

a radiation source (1) for emitting radiation which progresses through the first window (3a), the sample chamber (2) and further through the second window (3b);

one or a plurality of detectors (9, 9a, 9b) which is or are optically directed toward said second window or window section;

an optical filter (8, 8a, 8b) between said opening of the second window and each detector; and a wave tube (7; 7a, 7b) located between the second sample chamber window (3b) or window section and the detector (9a, 9b) and comprising an envelope made of a solid material (18), provided with radiation transmissive ends (15, 16) and an interior (11) having a radiation reflective inner surface (17);

wherein said optical filter is an interference filter (8, 8a, 8b) transmissive to a certain wavelength band, wherein said envelope material (18) has an index of refraction which exceeds that of the wave tube interior (11), and wherein the wave tube has a length (LL) which is at least about five times its mean diameter (D; D1 or D2) for carrying the radiation emitted from the chamber along the wave tube to each detector (9, 9a, 9b), whereby the radiation directed to a detector comprises that which is incident on said interference filter (8, 8a, 8b) at angles of incidence on the filter smaller than 10°.

2. A measuring sensor as set forth in claim 1, characterized in that the number of filters and detectors (8a and 9a; 8b and 9b . . . ) is respectively at least two, arranged pairwise with one filter for one detector and located side by side relative to the radiation emitting through the second window (3b), said wave tube carrying the radiation emitted from the sample chamber (2) along a plurality of tubes (7a, 7b . . . ) in a substantially equal manner to each detector, and that the filters (8a, 8b, . . . , 8i . . . ) included in said filter-detector pairs are located either at the wave tube end (16) adjacent to the detector or at the end (15) thereof adjacent to the sample chamber or as an actual second window (3b) fitter in the window opening of the sample chamber.

3. A measuring sensor as set forth in claim 2, characterized in that the measuring sensor is provided with a plurality of filters and detectors 8a and 9a; 8b and 9b . . . ) as combinations for identifying the type and/or for determining the concentration of a plurality of components included in a medium to be analyzed and that all detectors (9a, 9b, 9c . . . ) are engaged with the same element (18 or 20) having a high thermal conductivity for maintaining said detectors at a constant and/or controlled temperature.

4. A measuring sensor as set forth in claim 1, characterized in that the wave tube (7; 7a, 7b) is cylindrical in its cross-section and its cross-sectional surface corresponds roughly to the cross-sectional outlet surface area of the second window (3b) or is smaller than this cross-sectional outlet surface area.

5. A measuring sensor as set forth in claim 1, characterized in that the wave tube (7; 7a, 7b) is converging from the second window (3b) towards each detector (9a, 9b).

6. A measuring sensor as set forth in claim 1, characterized in that the wave tube (7; 7a, 7b) is diverging from the second window (3b) towards each detector (9a, 9b).

7. A measuring sensor as set forth in claim 1, characterized in that each detector (9a, 9b) is provided with its own, at least partially separate, wave tube (7a, 7b) and that these lengths (LL) of separate wave tubes form a small angle (K) relative to each other, the bisector of said angle being orthogonal to the plane of the second window (3b).

8. A measuring sensor as set forth in claim 1, characterized in that each detector (9a, 9b) is provided with its own, at least partially separate wave tube (7a, 7b) and that these separate wave tubes, when progressing from the second window (3b) towards each detector (9), curve outwardly from a median normal of said second window.

9. A measuring sensor as set forth in claim 1, characterized in that the ratio of said wave tube length (LL) to the mean diameter (D; D1 or D2) is in the order of 10–30, and that the wave tube centerline is at least approximately orthogonal to the plane of said interference filter.

10. A measuring sensor as set forth in claim 1, characterized in that the wave tube (7; 7a, 7b) consists of a hole (11) made in a solid material (18) provided with an inner surface (17) which is polished to be radiation reflective and which includes ends (15, 16) directed towards the said sample chamber (2) and said detector (9a, 9b) respectively, and that the solid material comprises a metal or a solid non-metal or some polymeric material, glass, or mineral, having an index of refraction which exceeds that of the wave tube interior (11).

11. A measuring sensor as set forth in claim 10, characterized in that the volume (11) formed by the interior of said wave tube (7; 7a, 7b) contains a gas or gas mixture at a reduced pressure, or a gas or gas mixture or some other medium at a positive pressure, and that the gas or gas mixture comprises air, some other gas or gas mixture or, the medium within the wave tube contains the gas or medium which is included as an interfering component in a gas mixture or medium to be analyzed and contained in the sample chamber.

12. A measuring sensor as set forth in claim 1 characterized in that the volume (11) formed by the interior of said wave tube (7; 7a, 7b) contains a gas or gas mixture at a reduced pressure, or a gas or gas mixture or some other medium at a positive pressure, and that the gas or gas mixture comprises air, some other gas or gas mixture or, the medium within the wave tube contains the gas or medium which is included as an interfering component in a gas mixture or medium to be analyzed and contained in the sample chamber.

13. A measuring sensor as set forth in claim 12, characterized in that the inlet end (15) of the wave tube (7; 7a, 7b) corresponding to each detector is focused on the surface region of the second window (3b) or first window (3a) or radiation source (1) for delivering the same radiation intensity into each wave tube and further to the detector (9, 9a, 9b).

14. A measuring sensor as set forth in claim 1, characterized in that the measuring sensor is provided with a plurality of filters and detectors (8a and 9a; 8b and 9b . . . ) as combinations for identifying the type and/or for determining the concentration of a plurality of components included in a medium to be analyzed and that all detectors (9a, 9b, 9c . . . ) are engaged with the same element (18 or 20) having a high thermal conductivity for maintaining said detectors at a constant and/or controlled temperature.

15. A measuring sensor as set forth in claim 1, characterized in that the inlet end (15) of the wave tube (7; 7a, 7b) corresponding to each detector is focused on the surface region of the second window (3b) or first window (3a) or radiation source (1) for delivering the same radiation intensity into each wave tube and further to the detector (9, 9a, 9b).

16. A measuring sensor as set forth in claim 1, characterized in that the reflective inner surface (17) of said wave tube, or respectively wave tubes (7, 7a, 7b), consists of an interference mirror coating (27) and that said transmissive wavelength band of the interference filter (8, 8a, 8b . . . ) is selected in accordance with a predetermined component of the sample medium to be analyzed.

17. A measuring sensor as set forth in claim 1, characterized in that, in the direction transverse to a principal traveling direction (R) of the radiation, said radiation source (1) has a relatively large surface which is approximately equal to the surface area of the first window (3a) of the sample chamber (2).

18. A measuring sensor for the spectroscopic analysis of mediums, said measuring sensor comprising:

a sample chamber (2) for a medium to be analyzed, said chamber being provided with at least two radiation transmitting windows (3a, 3b) or window sections in window openings included in the chamber;

a radiation source (1) for emitting radiation which progresses through the first window (3a), the sample chamber (2) and further through the second window (3b);

a plurality of detectors (9, 9a, 9b) which are optically directed towards this second window or window section;

an optical filter (8, 8a, 8b) between said opening of the second window and each detector; and a wave tube located between the second sample chamber window (3b) or window section and each detector (9a, 9b) and comprising an envelope made of a solid material (18), provided with radiation transmissive ends (15, 16) and an interior (11) having a radiation reflective inner surface (17);

wherein each optical filter is an interference filter (8, 8a, 8b) transmissive to a certain wavelength band and positioned adjacent one of said detectors, wherein said solid envelope material (18) has an index of refraction which exceeds that of the wave tube interior (11), wherein each wave tube has a length (LL) which is at least about five times its mean diameter (D or DD), and wherein the measuring sensor comprises at least two wave tubes (7a, 7b . . . 7i), each of which carrier radiation from the second window (3b) towards one of the detectors (9a, 9b, . . . 9i) and which form a small angle (K) relative to each other so that said radiation impinges on each interference filter (8, 8a, 8b . . . 8i) as a set of beams, the beams having an average angle of incidence on the respective filter of less than 10°.

19. A method for the spectroscopic analysis of mediums by means of a measuring sensor, comprising a sample volume (2) for a medium to be analyzed, said volume including at least two surface sections (3a, 3b) transmissive to the radiation employed in the spectroscopic analysis, a radiation source (1) emitting radiation which travels through a first surface section (3a), the sample volume (2) and a second surface section (3b), through a wave tube (7; 7a, 7b) located after the sample volume and provided with an inner surface (17) reflecting radiation towards the interior of the tube, and through a respective optical filter (8, 8a, 8b) located between the second surface section and one or more detectors (9, 9a, 9b), each detector being optically directed towards the second surface section, characterized in that after the second surface section (3b) the radiation is allowed to propagate through at least one wave tube (7; 7a, 7b . . . ), a material (18) forming a reflective inner surface (17) of said wave tube having an index of refraction which exceeds that of the wave tube interior (11), such portion of the radiation, whose angular distribution includes an angle of advance (R+/−) of the radiation exceeding about +/−20°, is allowed to reflect from this inner surface (17) of the wave tube at least three times in the propagating direction of radiation, for reducing the introduction of this portion of radiation into the detector, and the radiation is allowed to propagate through the optical filter comprising a wavelength band transmissive interference filter (8, 8a, 8b . . . ) either upstream or downstream of the wave tube and, finally, the filtered radiation is allowed to impinge on the respective detector for producing an electrical signal indicative of the spectroscopic properties of the medium being analyzed.

\* \* \* \* \*